United States Patent [19]

Moldenhauer

[11] 4,282,326

[45] Aug. 4, 1981

[54] CELL CULTURE MEDIUM SUPPLEMENT

[76] Inventor: Jeanne Moldenhauer, Rte. 2, Box 361A, Long Grove, Ill. 60047

[21] Appl. No.: 51,248

[22] Filed: Jun. 22, 1979

Related U.S. Application Data

[63] Continuation-in-part of Ser. No. 950,748, Oct. 12, 1978, abandoned.

[51] Int. Cl.$^3$ ............................................. C12N 5/00
[52] U.S. Cl. ................................................. 435/240
[58] Field of Search .................... 435/240, 241, 1; 195/1.7, 1.8; 252/408

[56] References Cited

U.S. PATENT DOCUMENTS

| | | | |
|---|---|---|---|
| 3,432,595 | 3/1969 | Kasza | 435/240 X |
| 3,574,137 | 4/1971 | Decasperis | 252/408 |
| 3,850,748 | 11/1974 | Cook et al. | 435/241 |
| 3,862,002 | 1/1975 | Sanders | 435/240 X |
| 4,049,494 | 9/1977 | Tomei | 435/240 X |
| 4,098,646 | 7/1978 | Jones et al. | 435/240 |
| 4,102,810 | 7/1978 | Armstrong | 252/408 |

OTHER PUBLICATIONS

Parker, *Methods of Tissue Culture,* Harper & Row, New York, 1964, 57, 58, 72–75.
Rose et al., *The Condensed Chemical Dictionary,* 7th Edition, Reinhold Book Corporation, New York, 1967, pp. 779 and 872.
Mizrahi, *Biotechnology and Bioengineering,* XIX (1977), 1557–1561.
Humko Sheffield Technical Bulletin, "Primatone RL," Primatone G, and Primatone HS, Sep. 1977.

*Primary Examiner*—Esther M. Kepplinger
*Attorney, Agent, or Firm*—Cook, Wetzel & Egan, Ltd.

[57] ABSTRACT

An improved cell culture medium supplement comprising a sterile solution of Dulbecco's phosphate buffered saline solution along with amino acids of such constitution and concentration sufficient to supplement growth of the cells to be cultured, and whereby the cell culture medium properties of blood serum are simulated.

5 Claims, No Drawings

CELL CULTURE MEDIUM SUPPLEMENT

BACKGROUND OF THE INVENTION

This application is a continuation-in-part of application Ser. No. 950,748 filed on Oct. 12, 1978 now abandoned.

The present invention relates in general to cell culture media and more particularly to an improved cell culture medium supplement which simulates the cell culture medium properties of blood serum.

Various different blod sera have been utilized in the culture of various types of cells. Because of the various problems associated with the use of such sera, one suggested approach has been the partial or total replacement thereof.

One such attempt at the partial or total replacement of sera is reported at Vol. XIX, *Biotechnology, and Bioengineering* (1977), and entitled "Primatone RL in Mammalian Cell Culture Media." Although these and other efforts have proved satisfactory in some cases and for limited applications, the results were not satisfactory in many other cases.

Another approach has been to completely replace the entire cell culture medium rather than to attempt to partially replace sera as a medium supplement. This approach is set forth in U.S. Pat. No. 4,049,494 to Tomei. Tomei's medium is a clinically defined culture media for the cultivation of BHK-6 cells, which are in turn used to produce a vaccine. As such, Tomei's medium is a completely chemically defined cultured media which is specific for one particular type of cells only and cannot be utilized as a medium for a wide variety of cells. This feature of Tomei's medium is particularly disadvantageous. An additional disadvantage of Tomei's medium is that, because it is a completely defined chemical culture media, its use would require radical change from any media currently in use. Accordingly, a researcher in order to use Tomei's medium in a continuing specific experiment would have to adapt, if possible, the cell line to this new medium.

An additional disadvantage of Tomei's medium is that it has a pH of 4.3, which is unsuitable for most cell lines, and in general would in fact be cytotoxic. In contrast, standard commercially available media for mammalian cell lines or cell strains (heteroploid-diploid) range in pH from 6.5 to 7.4. Commercially available serum is expected to have a pH of approximately 7.0–7.1. Accordingly, Tomei's medium would in general be unsuitable as well for use with all standard culture media.

A yet further disadvantage of Tomei's medium is that it contains sodium pyruvate, which is very labile and greatly decreases the shelf life of the medium. Moreover, Tomei's medium contains phenol red, which in some concentrations, has been shown to have cytotoxic effect to several cell lines.

It is accordingly an object of the present invention to provide an improved cell culture medium supplement which materially alleviates the disadvantages of prior art systems.

It is an additional object of the present invention to provide an improved cell culture medium supplement which may be used for a wide variety of cell lines and whose use will not necessitate extended adaption of a cell line to the medium as supplemented.

It is a further object of the present invention to provide an improved cell culture medium supplement which combines amino acids of such constitution and concentration sufficient to support growth in the cells to be cultured, with an appropriate quantity of Dulbecco's phosphate buffered saline, whereby the cell culture properties of blood serum are simulated.

SUMMARY OF THE INVENTION

The improved cell culture medium supplement of the present invention comprises a sterile solution of potassium chloride, potassium phosphate, sodium chloride, monobasic hydrated sodium phosphate, and various amino acids of such composition sufficient to support growth in the cells to be cultured, whereby the beneficial properties of blood serum in that respect are simulated. The amino acids preferably utilized in a preferred embodiment of the present invention are prepared by peptic digest of animal tissue and are available from Humko Sheffield Chemical, Division of Kraft, Inc., and sold under the trademarks Primatone RL, Primatone G, and Primatone HS.

In other preferred embodiments of the improved cell culture medium supplement of the present invention one or more of said amino acids may be radioactive, whereby the biological uptake of such amino acid may be monitored in the cells to be cultured. Yet additionally, a lipid may be added, whereby a lipidized serum is simulated. Yet further, calcium chloride and magnesium chloride may be added. Such latter embodiments are useful when splitting a culture of mammalian cells to inactivate the trypsin therein, so that a confluent monolayer of cells may be obtained, without serum addition.

The improved cell culture medium supplement of the present invention may be better understood by reference to the examples set forth hereinbelow.

DETAILED DESCRIPTION OF THE PREFERRED EMBODIMENTS

The following examples are illustrative of the composition and method of production of the improved cell culture medium supplement of the present invention.

EXAMPLE 1

This example illustrates some of the physical properties and the chemical composition by amino acid assay of Primatone RL in milligrams per gram, one of the amino acid compositions which may be preferably utilized in the present invention.

| Physical Properties | |
|---|---|
| Moisture | 3.7% |
| Total Nitrogen | 11.6% |
| Amino N/Total N | 49.3% |
| Chloride | 1.2% |
| pH (2% solution) | 7.2 |
| Solubility (clear, 30° C.) | 120 g/1000 cc |

| Amino Acid Assay | | | |
|---|---|---|---|
| Amino Acid | Amount (mg/g) | Amino Acid | Amount (mg/g) |
| Lysine | 48.0 | Alanine | 52.1 |
| Histidine | 20.1 | Cystine | Not calculable |
| Arginine | 26.5 | Valine | 48.4 |
| Aspartic Acid | 69.0 | Methionine | 14.8 |
| Threonine | 33.0 | Isoleucine | 24.5 |
| Serine | 35.6 | Leucine | 66.8 |
| Glutamic Acid | 85.1 | Tyrosine | 9.7 |
| Proline | 35.7 | Phenylalanine | 33.4 |
| Glycine | 45.9 | Tryptophan | 7.6 |

EXAMPLE 2

This example illustrates some of the physical properties and the chemical composition by amino acid assay of Primatone G in milligrams per gram, one of the alternative amino acid compositions which may be preferably utilized in the present invention.

| Physical Properties | |
|---|---|
| Total Nitrogen | 16.45% |
| Amino Nitrogen | 2.63% |
| pH, 2% solution | 7.0 |
| Color | Light Straw Color |
| Clarity | Sparkling Clear |
| Chlorides | 1.9% |
| Sodium | 1.7% |
| Microbiological Content: | |
| Standard Plate Count | Less than 10,000/gm. |
| Coliform | Negative on all samples tested. |
| Salmonella | Negative on all samples tested. |

| Amino Acid Assay | | | |
|---|---|---|---|
| Amino Acid | Amount (mg/g) | Amino Acid | Amount (mg/g) |
| Lysine | 38.0 | Alanine | 84.5 |
| Histidine | 8.2 | Cystine | Not calculable |
| Arginine | 77.7 | Valine | 22.1 |
| Aspartic Acid | 62.1 | Methionine | 10.1 |
| Threonine | 18.2 | Isoleucine | 14.0 |
| Serine | 37.4 | Leucine | 29.1 |
| Glutamic Acid | 97.9 | Tyrosine | 6.9 |
| Proline | 122.0 | Phenylalanine | 18.8 |
| Glycine | 194.0 | Tryptophan | <0.5 |

EXAMPLE 3

This example illustrates some of the physical properties and the chemical composition by amino acid assay of Primatone HS in milligrams per gram, one of the further alternative preferred amino acid compositions which may be preferably utilized in the present invention.

| Physical Properties | |
|---|---|
| Total Nitrogen | 12.15% |
| Amino Nitrogen | 4.93% |
| Moisture | 3.8% |
| pH, 2% solution | 7.1 |
| Color | Light Tan |
| Clarity, 2% solution | Sparkling Clear |

| Amino Acid Assay | | | |
|---|---|---|---|
| Amino Acid | Amount (mg/g) | Amino Acid | Amount (mg/g) |
| Lysine | 51.0 | Alanine | 52.5 |
| Histidine | 13.6 | Cystine | Not calculable |
| Arginine | 21.9 | Valine | 36.7 |
| Aspartic Acid | 65.4 | Methionine | 15.4 |
| Threonine | 31.0 | Isoleucine | 26.2 |
| Serine | 33.6 | Leucine | 54.8 |
| Glutamic Acid | 104.0 | Tyrosine | 10.2 |
| Proline | 50.2 | Phenylalanine | 25.3 |
| Glycine | 65.4 | Tryptophan | 3.3 |

EXAMPLE 4

Twenty liters of solution for use in the improved cell culture medium supplement of the present invention are made with the following ingredients:
Sodium chloride: 160 g/20 liters
Potassium chloride: 4 g/20 liters
Disodium phosphate $Na_2HPO_4$: 23 g/20 liters
Monobasic potassium phosphate $KH_2PO_4$: 4 g/20 liters The above items are weighed out and added in the above order to a 4 liter flask containing approximately 2 liters of deionized, doubled-distilled water. The flask is placed on a magnetic stirrer and stirred to facilitate solution of the above salts without heat. After all the above salts have been dissolved, the solution is brought up to volume with a further quantity of deionized, doubled-distilled water.

The pH is checked and then adjusted to 7.0 pH with 1 N HCl. The solution is then filtered through a sterile 293 nm filter pad or through a Gelman cartridge system, and then is aseptically collected into sterile bottles in a sterile hood. After all the solution has been sterilized, quality control samples are checked for sterility, virus and mycoplasma contamination using tests which meet FDA standards, such as nutrient broth, tryptic soy broth, blood agar plates, saubaroud's agar, and mycoplasma agar, as well as CPE tests on sensitive cell lines, human embryonic lung, kidney tissue, human embryonic foreskin, etc.

The above solution is stored at 4° C., but does not need to be refrigerated. Ten kilograms of amino acids are added to a large mixing vat. Approximately, 10 liters of the above salt solution are added to the amino acids while stirring. Then the rest of the above salt solution is added to the vat to bring the mixture to its final volume.

In some instances it may be necessary to stir the mixture for about 20 to 30 minutes before total dissolution appears. The solution is then checked for pH and buffering capacity. It is then membrane filtered through a sterile 293 nm stack of membrane filter pads or through a cartridge system using an aseptic fill and a sterile hood. It should be noted that membrane sterilization is not necessary because the solution is autoclavable. However, in certain preferred embodiments membrane filter elements may be used to guarantee that there are no particles greater than 0.22 microns left in the solution. Batch samples are kept and quality control samples are checked for cytotoxicity, growth promotion and sterility. After passing such tests, the solution is ready for use.

EXAMPLE 5

The above procedure of Example 4 is repeated, except that 1.0 gram per liter of magnesium chloride is added.

EXAMPLE 6

The procedure of Example 5 is repeated, except the 2 grams per liter of calcium chloride are also added.

EXAMPLE 7

The procedure of Example 6 is followed. The buffering capacity of the solution is checked and the osmolarity found to be about 300, i.e., within the physiological limits, or is adjusted to 300 milli osmoles.

EXAMPLE 8

The procedure of Example 4 is followed and utilized in the culture of mammalian cells. Prior to the culture of cells being split, 10% serum is added to inactivate the trypsin present in order to obtain a confluent monolayer of cells. (Other non-serum proteins may be added to inactivate the trypsin: Casein, bovine serum albumin or Lactalbumenhydrolysate).

EXAMPLE 9

Sodium chloride: 160 g/20 liters
Potassium chloride: 4 g/20 liters
Disodium phosphate $Na_2HPO_4$: 23 g/20 liters
Monobasic potassium phosphate $KH_2PO_4$: 4 g/20 liters The above items are weighed out and added in the above order to a 4-liter Erlenmeyer flask of distilled-deionized water. The salts are dissolved with stirring, without heat to form a first salt solution.

Calcium chloride: 20 g/20 liters (anhydrous).
Magnesium chloride: 20 g/20 liters $(C.6H_2O)$.

The above ingredients are weighed out and dissolved in 2 liters distilled-deionized water, and then stirred without heat until dissolved to form a second salt solution. The above first and second salt solutions are combined.

L-cystine: 0.01 g/20 liters
L-tyrosine: 97 g/20 liters

The above ingredients are weighed out above and added to 2 liters distilled-deionized water. The mixture is stirred on a magnetic stirrer, adding NaOH (sodium hydroxide) tablets one at a time to facilitate dissolving. When dissolved, the above amino acid solution is added to the combined salt solution.

Lysine: 480 g/20 liters
Histidine: 201 g/20 liters
Arginine: 265 g/20 liters
Aspartic Acid: 690 g/20 liters
Threonine: 330 g/20 liters
Serine: 356 g/20 liters
Glutamic Acid: 851 g/20 liters
Proline: 357 g/20 liters
Glycine: 459 g/20 liters
Alanine: 521 g/20 liters
Valine: 484 g/20 liters
Methionine: 148 g/20 liters
Isoleucine: 245 g/20 liters
Leucine: 558 g/20 liters
Phenylalanine: 334 g/20 liters
Tryptophan: 76 g/20 liters The above amino acids are weighed out and added to the above salt and amino acid solution. The volume is brought up to 15 liters with distilled-deionized water, and stirred until dissolved.

The volume is brought up to 20 liters with distilled-deionized water.

The pH is checked and adjusted to 7.0 with 1 N HCl. The solution is then sterile filtered through a filter pad or cartridge system and is aseptically collected into sterile containers in a sterile hood.

Quality control samples are tested in compliance with FDA regulations and for ability to grow and maintain swine testicle (ST) cell lines without addition of serum.

The cell culture medium supplement of the present invention is stored at 4° C. until heat stability and sterility are checked.

Yet additionally, the calcium chloride and magnesium chloride may be eliminated if calcium ion and magnesium ion concentration are critical for a specific user.

The applicant's cell culture medium supplement of the present invention is being marketed under the trademark SEREX, and the following EXAMPLES 10-16 demonstrate the effectiveness of SEREX in reducing or replacing serum in cell culture media for use with regard to several different types of cells.

EXAMPLE 10

Primary pekin embryo fibroblast cells are disposed into 35×10 mm six well tissue culture plates (FB-6-TC) supplied by Linbro Chemical Company, Inc. The growth medium utilized was medium 199 with Hank's salts, sodium bicarbonate, L-glutamine (ISI: Gibco) and gentamicin 100 µg/ml (Scherring).

When the growth medium was supplemented with 10% SEREX, the cells grew at a rate comparable to the growth rate produced when 10% fetal bovine serum is used. Using 10% SEREX, confluency did not occur. When 9% SEREX and 1% serum was used, confluency and normal growth occurred.

The normal maintenance media was supplemented with 2%-5% fetal bovine serum as a growth media. When 5% SEREX was substituted for the fetal bovine serum, the cells could be maintained in the normal fashion. They could be maintained for up to 10 days without needing growth media. The cells were in good condition using SEREX only.

EXAMPLE 11

Porcine kidney cell line (PK15) cells were disposed into wells in plastic tissue culture plates having an area of two square centimeters. The Minimum Essential Media (MEM) with antibiotics was added.

The following chart sets forth the growth of such porcine kidney cell line cells utilizing SEREX and/or fetal calf serum (FCS):

| % SEREX or FCS | 1 day after seeding | 3 days after seeding |
|---|---|---|
| 10% SEREX only | 100% OK | 100% OK |
| 5% SEREX only | 95% OK | 100% OK |
| 4% SEREX only | 60% weak | not confluent |
| 5% SEREX-5% FCS | 100% OK | 100% OK |
| 5% FCS | 100% OK | 100% OK |
| 10% FCS | 100% OK | 100% OK |

The following chart sets forth the maintenance of such porcine kidney cell line cells using 3 day old monolayers grown to confluency with minimum essential media (MEM) utilizing 10% fetal calf serum or 10% SEREX.

| % SEREX or FCS | 2 days after changing to maintenance medium | 8 days after changing |
|---|---|---|
| 5% SEREX only | healthy & confluent | some floating dead cells, healthy confluent cells |
| 5% FCS | same as above | same as above |
| 10% SEREX | same as above | same as above |

EXAMPLE 12

The following data sets forth the growth of vero cells using varying concentrations of SEREX and/or fetal calf serum (FCS):

| % SEREX or FCS | 1 day after seeding | 3 days after seeding |
|---|---|---|
| 5% SEREX only | 5-10% granular weak looking | all dead except a few scattered cells |
| 9.2% SEREX only | same as above | same as above |
| 4.2% SEREX 0.83% FCS | 50% granular vacuolated | 95% rough looking, granular |

-continued

| % SEREX or FCS | 1 day after seeding | 3 days after seeding |
|---|---|---|
| 8.3% SEREX | 60% granular | 90% granular |
| 8.3% FCS | 100% OK | 100% OK |
| 0.9% SEREX | | |
| 10% FCS only | 100% OK | 100% OK |

The following chart sets forth the maintenance data of vero cells wherein 2 day old monolayers are grown to confluency using M199 and 10% fetal calf serum. The growth medium is discarded and replaced by M199 with SEREX and/or fetal calf serum.

| % SEREX or FCS | 2 days after changing to maintenance medium | 8 days after changing to maint. medium |
|---|---|---|
| 10% FCS only | healthy & confluent | floating dead cells over thick layers of healthy confluent cells |
| 5% FCS only | healthy & confluent | same as above |
| 9% SEREX 1% FCS | healthy & confluent | 50% round dead cells; remainder contracting, moribund |
| 10% SEREX only | all cells thin, contracting | 30% round dead cells; remainder contracting, moribund |

EXAMPLE 13

The following chart sets forth the growth pattern utilizing SEREX and/or fetal calf serum for swine testicle cell line:

| % SEREX or FCS | 1 day after seeding | 3 days after seeding |
|---|---|---|
| 10% FCS | 100% OK | 100% OK |
| 5% FCS-5% SEREX | 100% OK | 100% OK |
| 5% SEREX | healthy; fewer than above | healthy; 90% confluent |
| 10% SEREX | 100% OK | 100% OK |

Three day old monolayers of swine testicle cell line were grown with 10% fetal calf serum. The following chart sets forth the maintenance results of partial and/or complete replacement of fetal calf serum with SEREX.

| % SEREX or FCS | 2 days after changing to maintenance medium | 8 days after changing |
|---|---|---|
| 10% FCS | healthy & confluent | healthy % confluent |
| 5% FCS | " | " |
| 5% FCS-5% SEREX | " | " |
| 3% FCS | " | " |
| 5% SEREX | " | " |
| 10% SEREX | " | " |

EXAMPLE 14

The following chart represents the growth pattern of Embryonic Mule Skin (EMS) utilizing Hank's Medium 199 with SEREX and/or fetal calf serum:

| % SEREX or FCS | 1 day after seeding | 30 days after seeding |
|---|---|---|
| 10% FCS | 100% OK | 100% OK |
| 5% FCS | healthy, reduced | 100% OK |
| 5% SEREX only | 50% dead, growth weak | 95% dead or weak |
| 10% SEREX-5% FCS | 100% OK | 100% OK |

The following chart sets forth the maintenance pattern obtained using Embryonic Mule Skin cells:

| % SEREX or FCS | 2 days after changing to maintenance medium | 5 days after changing |
|---|---|---|
| 10% FCS | 100% OK | 100% OK |
| 5% FCS-5% SEREX | 100% OK | 100% OK |
| 10% SEREX | 100% OK | reduced growth |

EXAMPLE 15

The following chart illustrates the growth of Roswell Park Memorial Institute (RPMI) 8226 cell line, a human lymphocyte cell line, utilizing RPMI 1640 as a medium:

| % SEREX or FCS | 1 day after seeding | 3 days after seeding |
|---|---|---|
| 20% FCS | healthy 100% OK | confluent monolayer |
| 10% FCS | " | 100% OK |
| 5% FCS-5% SEREX | " | 100% OK |
| 4% FCS-6% SEREX | " | 100% OK |
| 3% FCS-7% SEREX | 100% OK | 100% OK |
| 2% FCS-8% SEREX | 100% OK | 100% OK |
| 1% FCS-9% SEREX | healthy, reduced number | no confluence 50% dead |
| 10% SEREX only | weak, slow growth | 60% dead, weak |

The following chart illustrates the maintenance patterns obtained for the RPMI cell line using SEREX and/or fetal calf serum:

| % SEREX or FCS | 2 days after changing to maintenance medium | 5 days after changing to maint. medium |
|---|---|---|
| 2% FCS | healthy & confluent | 100% OK |
| 5% FCS | " | " |
| 1% FCS | healthy, 100% OK | some dying, weak |
| 1% FCS-5% SEREX | healthy & confluent | 100% OK |
| 5% SEREX | healthy & confluent | some dying, weak |

EXAMPLE 16

The following chart sets forth the growth of L929 (mouse) cells grown in minimum essential media (MEM) with Earles Salts with L-glutamine.

| % SEREX or FCS | 1 day after seeding | 3 days after seeding |
|---|---|---|
| 10% FCS | healthy 100% OK | 100% OK |
| 9% FCS-1% SEREX | " | " |
| 8% FCS-2% SEREX | " | " |
| 7% FCS-3% SEREX | " | " |
| 6% FCS-4% SEREX | " | " |
| 5% FCS-5% SEREX | " | " |
| 4% FCS-6% SEREX | " | " |
| 3% FCS-7% SEREX | " | " |
| 2% FCS-8% SEREX | weak, contracting | 50% dead |
| 1% FCS-9% SEREX | 10% dead, weak | 70% dead |
| 10% SEREX | some suspended cells | 95% dead, weak |

In regard to maintenance, 3 day old monolayers of L929 cells were cultured using 10% fetal calf serum. The same concentrations used as growth media were used for the maintenance media. As little as 3% fetal calf serum and 7% SEREX were able to maintain the cells for 5-7 days.

The above examples are meant to be illustrative of the embodiments of the present invention and no limitation is intended thereby.

The percentages of ingredients by dry weight of the composition of Example 4 are, as follows:

| Ingredient | % (by dry weight) |
|---|---|
| potassium chloride | 0.336 |
| monobasic potassium phosphate | 0.336 |
| sodium chloride | 13.4 |
| dibasic sodium phosphate | 1.93 |
| amino acids of such composition sufficient to support growth in the cells to be cultured | 84.0 |

The 84.0% by dry weight of amino acids of such composition sufficient to support growth in the cells to be cultured, where Primatone RL is used as the source of the amino acids, is calculated as follows from the assay of Example 1:

L-cystine-trace
L-tyrosine 1.26%
Lysine 6.25%
Histidine 2.62%
Arginine 3.45%
Aspartic Acid 8.96%
Threonine 4.30%
Serine 4.75%
Glutamic Acid 11.08%
Proline 4.65%
Glycine 5.98%
Alanine 6.78%
Valine 6.30%
Methionine 1.93%
Isoleucine 3.19%
Leucine 7.26%
Phenylalanine 4.35%
Tryptophan 0.99%

The 84.0% by dry weight of amino acids of such composition sufficient to support growth in the cells to be cultured, where Primatone G is used as the source of the amino acids, is calculated as follows from the assay of Example 2:

L-cystine-trace
L-tyrosine 0.69%
Lysine 3.79%
Histidine 0.89%
Arginine 7.76%
Aspartic Acid 6.20%
Threonine 1.82%
Serine 3.73%
Glutamic Acid 9.77%
Proline 12.18%
Glycine 19.37%
Alanine 8.43%
Valine 2.21%
Methionine 1.01%
Isoleucine 1.40%
Leucine 2.90%
Phenylalanine 1.88%
Tryptophan 0.05%

The 84.0% by dry weight of amino acids of such composition sufficient to support growth in the cells to be cultured, where primatine HS is used as the source of the amino acids, is calculated as follows from the assay of Example 3:

L-cystine-trace
L-tyrosine 1.30%
Lysine 6.45%
Histidine 1.73%
Arginine 2.79%
Aspartic Acid 8.38%
Threonine 3.94%
Serine 4.27%
Glutamic Acid 13.23%
Proline 6.38%
Glycine 8.38%
Alanine 6.68%
Valine 4.67%
Methionine 1.96%
Isoleucine 3.33%
Leucine 6.97%
Phenylalanine 3.22%
Tryptophan 0.42%

The percentage of ingredients by dry weight of Example 6 are, as follows:

| Ingredient | % (by dry weight) |
|---|---|
| potassium chloride | .335 |
| monobasic potassium phosphate | .335 |
| sodium chloride | 13.4 |
| dibasic sodium phosphate | 1.92 |
| calcium chloride | 0.167 |
| magnesium chloride | 0.167 |
| amino acids of such composition sufficient to support growth in the cells to be cultured | 83.7 |

These compositions and methods may be widely modified in the accordance with the principles and purposes of the present invention, one such purpose being to provide an improved cell culture medium supplement which is formulated from readily available ingredients.

In alternative preferred embodiments where a gel consistency is needed for collogen experimentation or chromatography, the Primatone G amino acid composition of Example 2 with its greater viscosity may be preferable. For other applications, such as where a slight color variation may be particularly useful as spectrophotometric and other color related experimentation, the Primatone HS of Example 3 is preferable.

Other modifications, substitutions and alternatives will be readily apparent to one skilled in the art upon a review of the present specification and are intended to be included within the scope of the invention.

What is claimed is:

1. A cell culture medium supplement comprising a solution of:
   approximately 0.336% by dry weight of potassium chloride;
   approximately 0.336% by dry weight of monobasic potassium phosphate;
   approximately 13.4% by dry weight of sodium chloride;

approximately 1.93% by dry weight of dibasic sodium phosphate; and
approximately 84.0% by dry weight of amino acids of such composition sufficient to support growth in the cells to be cultured, said amino acids comprising the following in approximate amounts:
L-cystine-trace
L-tyrosine 1.26%
Lysine 6.25%
Histidine 2.62%
Arginine 3.45%
Aspartic Acid 8.96%
Threonine 4.30%
Serine 4.75%
Glutamic Acid 11.08%
Proline 4.65%
Glycine 5.98%
Alanine 6.78%
Valine 6.30%
Methionine 1.93%
Isoleucine 3.19%
Leucine 7.26%
Phenylalanine 4.35%
Tryptophan 0.99%
whereby the cell culture medium properties of blood serum are simulated.

2. The cell culture medium supplement of claim 1 wherein at least one said amino acid is radioactive.

3. The cell culture medium supplement of claim 1 further comprising a lipid whereby a lipidized serum is simulated.

4. A cell culture medium supplement comprising a solution of:
approximately 0.336% by dry weight of potassium chloride;
approximately 0.336% by dry weight of monobasic potassium phosphate;
approximately 13.4% by dry weight of sodium chloride;
approximately 1.93% by dry weight of dibasic sodium phosphate; and approximately 84.0% by dry weight of amino acids of such composition sufficient to suppport growth in the cells to be cultured, said amino acids comprising the following in approximate amounts:
L-cystine-trace
L-tyrosine 0.69%
Lysine 3.79%
Histidine 0.89%
Arginine 7.76%
Aspartic Acid 6.20%
Threonine 1.82%
Serine 3.73%
Glutamic Acid 9.77%
Proline 12.18%
Glycine 19.37%
Alanine 8.43%
Valine 2.21%
Methionine 1.01%
Isoleucine 1.40%
Leucine 2.90%
Phenylalanine 1.88%
Tryptophan 0.05%
whereby the cell culture medium properties of blood serum are simulated.

5. A cell culture medium supplement comprising a solution of:
approximately 0.336% by dry weight of potassium chloride;
approximately 0.336% by dry weight of monobasic potassium phosphate;
approximately 13.4% by dry weight of sodium chloride;
approximately 1.93% by dry weight of dibasic sodium phosphate; and approximately 84.0% by dry weight of amino acids of such composition sufficient to support growth in the cells to be cultured, said amino acids comprising the following in approximate amounts:
L-cystine-trace
L-tyrosine 1.30%
Lysine 6.49%
Histidine 1.73%
Arginine 2.79%
Aspartic Acid 8.38%
Threonine 3.94%
Serine 4.27%
Glutamic Acid 13.23%
Proline 6.38%
Glycine 8.38%
Alanine 6.68%
Valine 4.67%
Methionine 1.96%
Isoleucine 3.33%
Leucine 6.97%
Phenylalanine 3.22%
Tryptophan 0.42%
whereby the cell culture medium properties of blood serum are simulated.

* * * * *